(12) United States Patent
Spring (10) Patent No.: US 10,918,593 B2
(45) Date of Patent: Feb. 16, 2021

(54) PERSONAL LUBRICANT DISK

(71) Applicant: Amy M. Spring, Divide, CO (US)

(72) Inventor: Amy M. Spring, Divide, CO (US)

(*) Notice: Subject to any disclaimer, the term of this patent is extended or adjusted under 35 U.S.C. 154(b) by 0 days.

(21) Appl. No.: 16/387,283

(22) Filed: Apr. 17, 2019

(65) Prior Publication Data

US 2019/0321288 A1 Oct. 24, 2019

Related U.S. Application Data

(60) Provisional application No. 62/659,239, filed on Apr. 18, 2018.

(51) Int. Cl.
*A61K 9/00* (2006.01)
*A61K 47/06* (2006.01)

(52) U.S. Cl.
CPC ............ *A61K 9/0034* (2013.01); *A61K 47/06* (2013.01)

(58) Field of Classification Search
CPC ..... A61K 9/0034; A61K 47/06; A61K 9/7007
See application file for complete search history.

(56) References Cited

U.S. PATENT DOCUMENTS

| | | | |
|---|---|---|---|
| 1,558,930 A | 10/1925 | Schuck | |
| 2,405,154 A | 8/1946 | Logan | |
| 5,169,251 A | 12/1992 | Davis | |
| 5,681,574 A | 10/1997 | Haber | |
| 6,578,205 B1 | 6/2003 | King | |
| 7,399,286 B2 | 7/2008 | Jackson | |
| 7,416,358 B2 | 8/2008 | Legendre | |
| 7,789,845 B1 | 9/2010 | Meliti | |
| 9,114,057 B1 | 8/2015 | Padilla | |
| 2002/0017310 A1 | 2/2002 | Gruenbacher | |
| 2007/0191320 A1* | 8/2007 | Yeager | A61K 9/0034 514/170 |
| 2011/0257474 A1 | 10/2011 | Howard | |
| 2011/0306942 A1 | 12/2011 | Thorpe | |
| 2012/0100195 A1 | 4/2012 | Sainz | |
| 2014/0157485 A1 | 6/2014 | Tarlian | |

(Continued)

FOREIGN PATENT DOCUMENTS

| | | |
|---|---|---|
| WO | WO0028939 A2 | 5/2000 |
| WO | WO2009060437 | 5/2009 |

OTHER PUBLICATIONS https://www.uhn.ca/PatientsFamilies/Health_Information/Health_Topics/Documents/Know_How_to_Use_Vaginal_Moisturizers_Lubricants.pdf Oct. 20, 2016.*

(Continued)

*Primary Examiner* — Blessing M Fubara
(74) *Attorney, Agent, or Firm* — Leyendecker & Lemire, LLC; Heather N. Tilley (57) ABSTRACT

A personal lubricant disk is described. The personal lubricant disk typically comprises a composition that is solid at ambient room temperature and melts into a liquid when placed and moved around the bodily surface of a human person. The composition of the personal lubricant disk typically comprises at least one of an emollient, a low melting point wax, a low melting point oil, and a water based lubricant. Variations of the personal lubricant disk composition can also include ingredients the stimulate different sensory reactions when the personal lubricant disk is placed and moved around the bodily surface, such as a warming or cooling sensation, as well as various pleasant tastes or scents.

13 Claims, 7 Drawing Sheets

(56) References Cited

U.S. PATENT DOCUMENTS

2016/0113866 A1* 4/2016 Kiser .................. A61K 35/747
 604/279
2017/0304016 A1 10/2017 Powell
2018/0136034 A1* 5/2018 Liebsch ................ B08B 15/023

OTHER PUBLICATIONS

2015 KY Liquibeads.*
Website Bezwecken.com and information concerning the Hydration Ovals product.
Screenshots from Amazon.com for hydration suppository products offered by Bezwecken including reviews with dates the reviews were provided.

* cited by examiner

PERSONAL LUBRICANT DISK

CROSS-REFERENCE TO RELATED APPLICATION

The present application claims the benefit of and priority to U.S. Provisional Patent Application No. 62/659,239, filed Apr. 18, 2018, entitled Lubricating Fingertip Disks and having the same inventor as the present application, the entire contents of which are hereby incorporated by reference.

BACKGROUND

Vaginal lubrication is important to a woman's overall health and sexual wellness. Normally, the natural lubrication of the vagina is created by the skin cells of the vagina and cervix under the influence of the female hormone, estrogen. Women with lower levels of estrogen therefore have minimal natural lubrication and experience vaginal dryness as a result. Vaginal dryness is often experienced by menopausal or post-menopausal women. However, vaginal dryness can be also be a common problem for pre-menopausal women with low levels of estrogen, such as breastfeeding mothers, women who have had a hysterectomy, women using birth control pills, and those undergoing or having undergone cancer radiation treatment.

Many women therefore use personal lubricants to temporarily reduce vaginal dryness as well as enhance their body's own natural lubrication. One of the problems that can result from a loss or reduction in the vagina's natural lubricant is experiencing pain or discomfort during sexual activity. The use of personal lubricants can help by minimizing the frictional forces that would otherwise cause irritation or tissue damage during sexual activity.

Personal lubricants are widely available, and are typically provided in bottles or squeeze tubes. However, the application of bottled and similarly packaged personal lubricants can be cumbersome, messy, and interrupt the otherwise natural flow of sexual intimacy.

DETAILED DESCRIPTION

Embodiments of the present invention comprise a lubricant disk generally sized to fit on the pad of a finger. The disk is typically solid at room temperature, and is designed to begin melting once placed in contact with the human body. Typically, the disk is placed on or near the external female genital tract. As the user moves the disk along or around the external female genital tract, the disk melts and releases a lubricant. Ideally, all or most of the disk will melt during use, and leave little or no unwanted residue on either the applying or receiving user.

The lubricant disks may be packaged in any suitable manner. For instance, the lubricant disks may be provided in a throat lozenge style tin container, for discreet transport. Alternatively, the disks may be individually contained in pre-formed plastic packaging, such as a blister pack, to prevent contamination of the unused disks. The disks may also be packaged with pre-moistened wipes, which may be used before or after the disk is used, if so desired.

The discreet and single-use design of the lubricant disk is tidier and more convenient to use than the commercial products currently available. Unlike personal lubricants provided in bottles or squeeze tubes, the lubricant disk provides the user with quantity control as each disk comprises a fixed quantity of lubricant. Further, the risk of undesirable leakage or spillage during transport is virtually eliminated, due to solid nature of the disk at room temperature. The lubricant disk also better facilitates the natural flow of sexual intimacy, as its methodology of use promotes emotional and physical intimacy.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "about," as used in this specification and appended claims, refers to plus or minus 20% of the value given.

The term "ambient room temperature," as used in this specification and appended claims, refers to the temperature of the surrounding air within the range of temperatures being suitable for human occupancy between 59 to 77 degrees Fahrenheit.

The term "approximately," as used in this specification and appended claims, refers to plus or minus 10% of the value given.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "disk," as used in this specification and appended claims, refers to a rounded thin plate of any shape.

The term "finger," as used in this specification and appended claims, refers to any of the five terminating members of the hand of a natural person, including the thumb.

The term "finger pad," as used in this specification and appended claims, refers to the fleshy underside of the end of a finger of a natural person.

The terms "generally" and "substantially," as used in this specification and appended claims, mean mostly, or for the most part.

The term "or" as used in this specification and the appended claims is not meant to be exclusive; rather the term is inclusive, meaning either or both.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

An Embodiment of a Personal Lubricant Disk

A personal lubricant disk 10 is illustrated in FIGS. 1-6. The first embodiment personal lubricant disk 10 is generally sized to fit on a finger pad of an adult person. Typically, the personal lubricant disk 10 is ovular in shape, typically no longer than one inch in length and three-quarters of an inch in width. In one variation, the personal lubricant disk 10 may be a circle, the circular shaped disk typically being no larger than one inch in diameter. In other variations, the personal lubricant disk 10 may be any other shape, including but not limited to a heart, diamond, square, or rectangle. When the personal lubricant disk 10 comprises a shape having a straight edge or edges that may otherwise form a sharp corner, the edges or corners of the disk are typically rounded, so as to not cause discomfort or pain when the personal lubricant disk 10 is moved around the surface of a human body.

Figure 1:
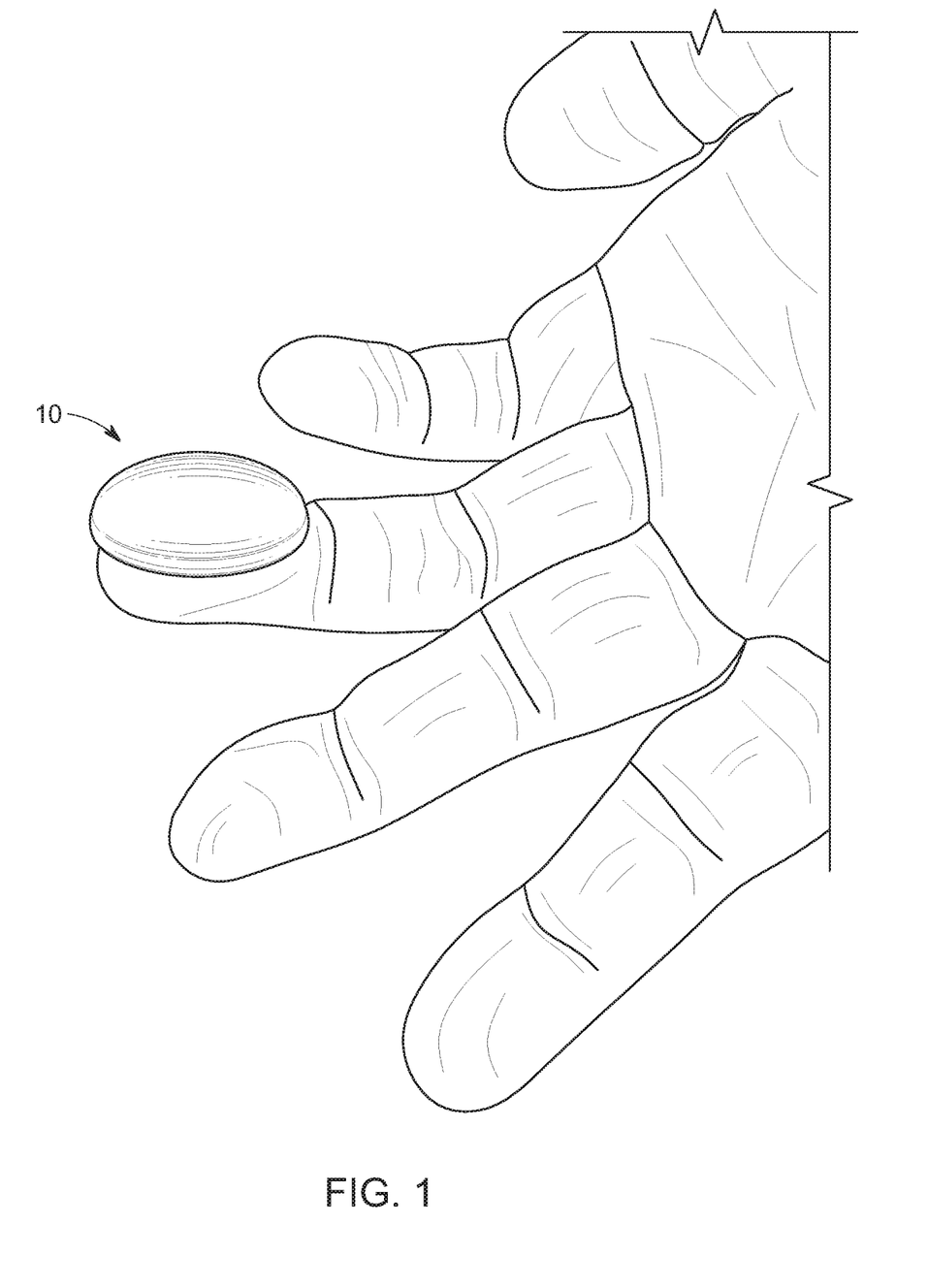
FIG. 1 is a perspective view of a personal lubricant disk received on a finger pad according to one embodiment of the present invention.
Figure 2:
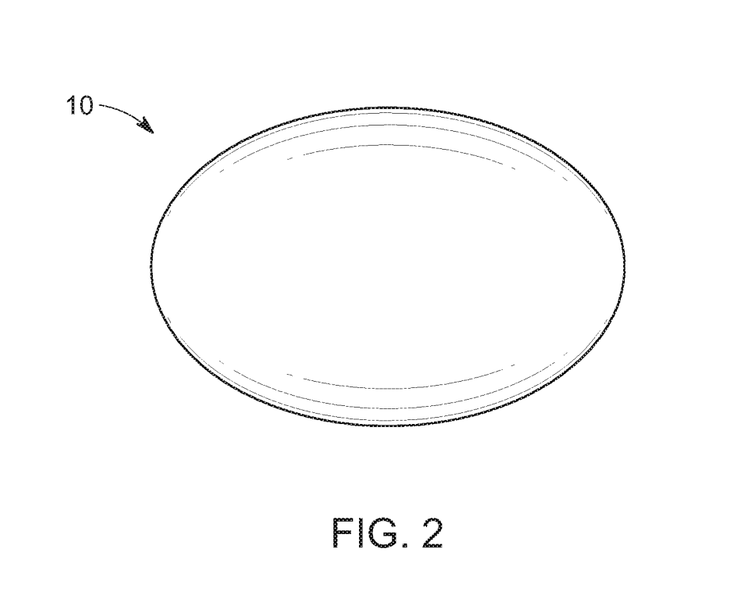
FIG. 2 is a top view of a personal lubricant disk according to one embodiment of the present invention.
Figure 3:
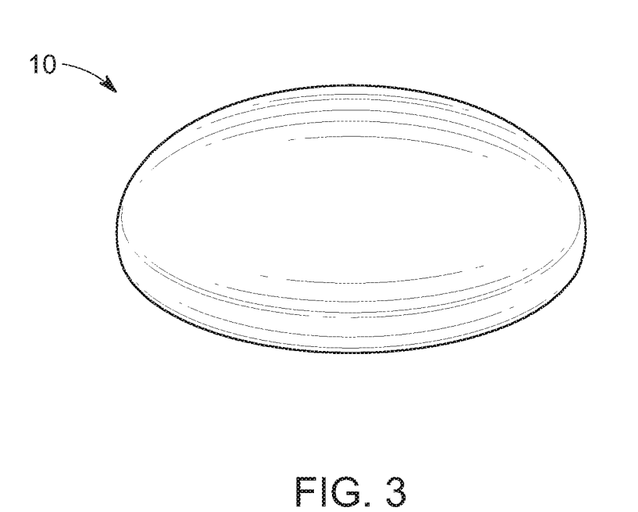
FIG. 3 is a perspective view of a personal lubricant disk according to one embodiment of the present invention.
Figure 4:
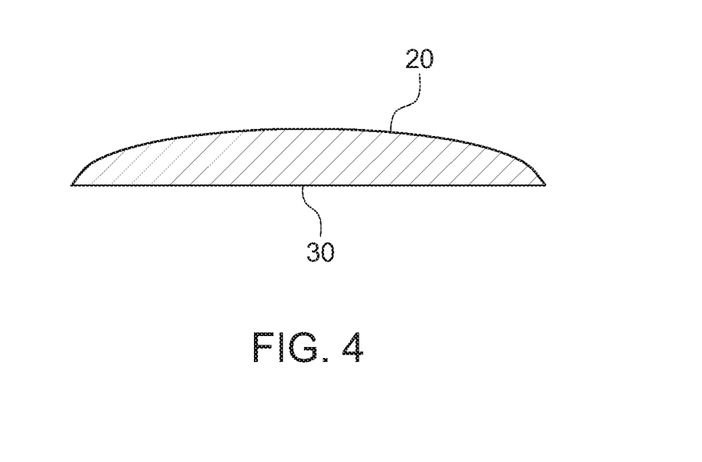
FIG. 4 is a cross-section view of a personal lubricant disk according to one embodiment of the present invention.
Figure 5:
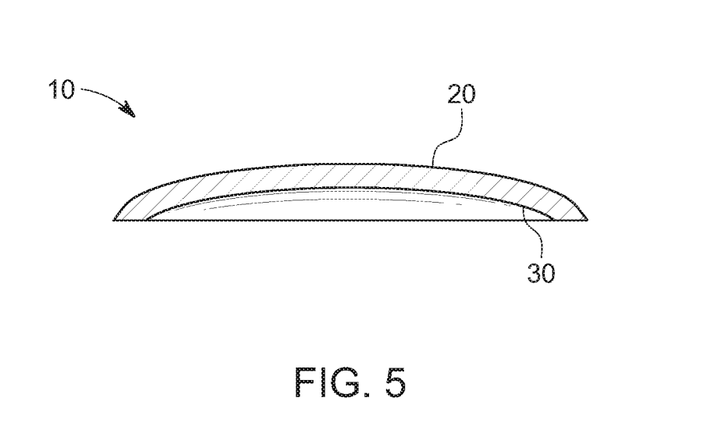
FIG. 5 is a cross-section view of a personal lubricant disk according to one embodiment of the present invention.

The personal lubricant disk 10 typically comprises a top side 20 and a bottom side 30. The personal lubricant disk 10 is typically received on a finger pad by placing the bottom side 30 on the finger pad, as shown in FIG. 1. The top side 20 is then placed on the bodily surface of the receiving user, typically on or around the external vaginal tract. Typically, the bottom side 30 is at least partially concave, so as to more comfortably rest on the finger pad. In another variation, the bottom side 30 may be flat, as seen in FIG. 4. In this variation, the bottom side 30 of the personal lubricant disk 10 typically forms around the finger pad as the personal lubricant disk 10 begins to melt.

The bottom side 30 and the top side 20 is typically substantially smooth, allowing for the personal lubricant disk 10 to be melted against the bodily surface of the receiving user with minimal resistance. In other variations, either or both the bottom side 30 and the top side 20 may provide a textured surface, such as small ridges or bumps. In variations wherein the bottom side 30 is textured, the textured surface helps prevent slippage of the bottom side 30 on the applying user's finger pad, thus helping keep the personal lubricant disk 10 in place on the applying user's finger pad as the personal lubricant disk 10 is melted on the bodily surface of the receiving user. In variations wherein the top side 20 is textured, the textured surface of the top side 20 provides additional stimulus when the personal lubricant disk 10 moved around the bodily surface of the receiving user.

The personal lubricant disk 10 typically comprises a composition that enables the personal lubricant disk 10 to be a solid at ambient room temperature and a liquid at temperatures of at least ninety degrees Fahrenheit, but not more than one-hundred degrees Fahrenheit. The preferred melting point of the personal lubricant disk 10 is between ninety-two degrees Fahrenheit and ninety-eight degrees Fahrenheit. The composition of the personal lubricant disk 10 typically comprises at least one of a low melting point oil, such as coconut oil, an emollient, such as illipe butter, a low melting point wax, such as beeswax, and a water-based lubricant, such as glycerin. In variations of the personal lubricant disk 10 wherein the composition at least partially comprises beeswax, it is preferable for the beeswax to make up no more than ten percent of the personal lubricant disk's total composition. This helps to limit residue that the personal lubricant disk 10 may leave on the bodily surface once the personal lubricant disk 10 has at least partially melted on such surface.

In one variation, the composition of the personal lubricant disk 10 may also include a flavorant additive, such as a natural strawberry flavoring. In this variation of the personal lubricant disk 10, the composition may also include a scent or coloring additive that is complimentary to the flavorant additive. For example, in variations wherein the personal lubricant disk 10 is strawberry flavored, the personal lubricant disk 10 composition may further comprise either or both a strawberry scented additive and a red coloring additive.

In another variation, the composition of the personal lubricant disk 10 may include a warming ingredient, such as glycerol, capsaicin, or an herbal extract. In this variation, the personal lubricant disk 10 may be a beneficial massaging aid, providing a warming sensation to the muscles of the receiving user as the personal lubricant disk 10 is melted and massaged into the receiving user's bodily surface. In other variations, the composition of the personal lubricant disk 10 may include a cooling ingredient, such as peppermint or eucalyptus.

In another variation, the composition of the personal lubricant disk 10 may include a contraceptive lubricant, such as a spermicide, to aid in the prevention of a pregnancy. In other variations, the composition of the personal lubricant disk 10 may include a soothing ingredient for skin irritation, such as aloe vera.

Typically, the personal lubricant disk 10 is a substantially uniform composition, wherein each component of the personal lubricant disk 10 composition is blended together to create a mixture. This mixture is typically created when the components are in a liquid state. The liquid mixture is then typically poured into a mold having the desired shape, and once cooled, the mixture forms a solid, creating the personal lubricant disk 10.

Figure 6:
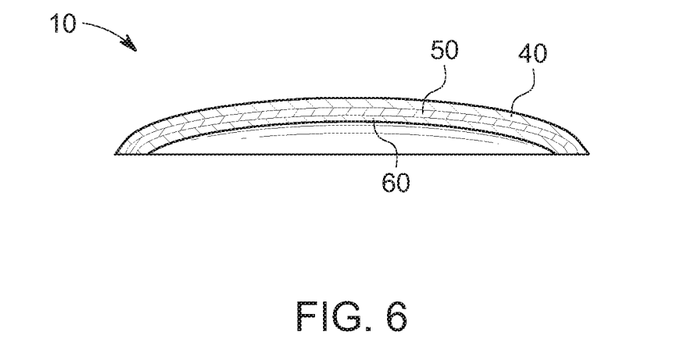
FIG. 6 is a cross-section view of a personal lubricant disk according to one embodiment of the present invention.

In another variation, the personal lubricant disk 10 comprises multiple layers of individual components 40-60, wherein each component of the personal disk composition remains a separate and distinct component, as illustrated in FIG. 6. In this variation, each individual component can be sprayed layer by layer into a mold having the desired shape, allowing each individual layer to cool and become a solid state before spraying the next layer. The layered variation of the personal lubricant disk 10 typically enables the bottom layer 60 to be comprised of a component having a higher melting point than the top layer 40, thereby allowing the top layer 40 to melt faster than the bottom layer 60, helping the bottom side 30 remain in place on the finger pad while the top side 20 of the personal lubricant disk 10 is applied and melted on a bodily surface.

The layered variation may also enable each component to provide a different sensation. For example, the bottom layer 40 may include a warming ingredient, the middle layer 50 may include a cooling ingredient, and the top layer 60 may include a flavorant additive. The layered variation typically comprises three layers; however, variations having between two and six layers are also contemplated.

Typically, the personal lubricant disk is used prior to sexual intercourse, and typically aids in providing vaginal lubrication. When used in this manner, the applying user sets the personal lubricant disk upon his or her preferred finger pad. The applying user then places the personal lubricant disk on or near the external female genital tract. As the applying user moves the personal lubricant disk along or around the external female genital tract, the personal lubricant disk begins to melt, thereby providing lubrication to the external female genital tract region. As the applying user continues to move the personal lubricant disk along or around the external female genital tract, the personal lubricant disk continues to melt, and in some instances, may also provide the stimulus necessary to encourage production of the female's natural vaginal lubrication. Ideally, all or most of the personal lubricant disk will melt during use, and leave little or no unwanted residue on either the applying or receiving user.

The personal lubricant disk 10 can be used for any suitable purpose. The single-use design of the individual personal lubricant disks 10 facilitates its portability and makes the personal lubricant disk 10 ideal for travel. This makes the personal lubricant disk 10 useful for a variety of purposes, such as for a travel sized hand or body moisturizer, as well as a travel sized lubricant to aid in shaving unwanted body or facial hair. Further, the single-use design enables the personal lubricant disk 10 to be individually packaged, allowing the user to easily control the quantity in which he or she travels with.

Figure 7:
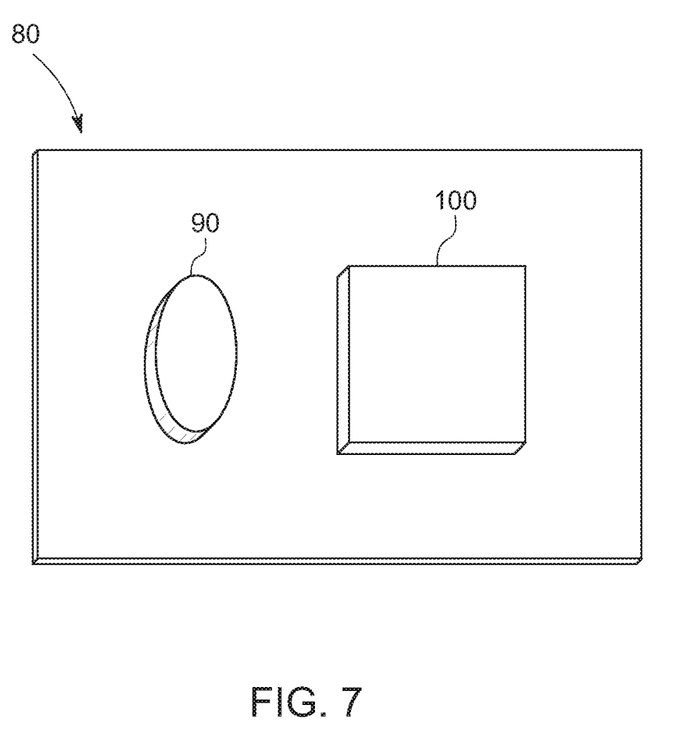
FIG. 7 is a top view of a personal lubricant disk provided in a pre-formed plastic packaging according to one embodiment of the present invention.

The personal lubricant disk 10 may be packaged in any suitable manner. Typically, the personal lubricant disk 10 is individually packaged in pre-formed plastic packaging, such as a blister pack, to prevent contamination of the other unused personal lubricant disks. In another variation, the personal lubricant disk 10 may be provided in a pocket-sized container, such as a throat lozenge tin, so as to facilitate discreet transport. In another variation, as seen in FIG. 7, the personal lubricant disk 10 may also be packaged with pre-moistened wipes or towelettes, which may be used to clean or sanitize the bodily area before or after the personal lubricant disk 10 is applied to such area, if so desired. In this variation, a blister pack duo 80 typically comprises a disk compartment 90 containing the personal lubricant disk 10, and a wipe compartment 100 containing a pre-moistened wipe or towelette.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A method of using a personal lubricant disk, the method comprising:
    providing the personal lubricant disk having a bottom side and a top side, the disk being substantially solid at ambient room temperature, and having a melting temperature of between 90-100 degrees Fahrenheit, the disk being sized to be received on a finger pad of an adult person and substantially contained within the boundaries of the finger pad;
    receiving the bottom side of the personal lubricant disk on the finger pad of an applying user;
    placing the top side of the personal lubricant on an external vaginal tract of a female user;
    moving the personal lubricant disk while received on the finger pad across the external vaginal tract thereby allowing the personal lubricant disk to melt; and
    lubricating the external vaginal tract with the personal lubricant disk until the personal lubricant disk is at least substantially melted.

2. The method of claim 1 further comprising removing the personal lubricant disk from a blister packaging unit.

3. The method of claim 1 further comprising removing the personal lubricant disk from a pocket-sized container.

4. The method of claim 1 further including producing natural vaginal lubrication by the female user in response to said moving the personal lubricant disk while received on the finger pad across the external vaginal tract.

5. The method of claim 1 wherein the personal lubricant disk further includes a flavoring agent.

6. The method of claim 1 wherein the personal lubricant disk includes a cooling ingredient and further comprises providing a cooling sensation to the external vaginal tract when the personal lubricant disk is moved across the external vaginal tract.

7. The method of claim 1 wherein the personal lubricant disk includes a warming ingredient and further comprises providing a warming sensation to the external vaginal tract when the personal lubricant disk is moved across the external vaginal tract.

8. The method of claim 1 wherein the bottom side is at least partially concave.

9. The method of claim 1 wherein the top side is at least partially convex.

10. The method of claim 8 wherein the top side is at least partially convex.

11. A method of using a personal lubricant disk, the method comprising:
    providing the personal lubricant disk having a concave bottom side and a convex top side, the disk being substantially solid at ambient room temperature, and having a melting temperature of between 90-100 degrees Fahrenheit, the disk being sized to be received on a finger pad of an adult person and substantially contained within the boundaries of the finger pad;
    removing the personal lubricant disk from packaging,
    receiving the bottom side of the personal lubricant disk on the finger pad of an applying user;
    placing the top side of the personal lubricant disk on an external vaginal tract of a female user;
    moving the personal lubricant disk while received on the finger pad across the external vaginal tract thereby allowing the personal lubricant disk to melt;

lubricating the external vaginal tract with the personal lubricant disk until the personal lubricant disk is at least partially melted; and producing natural vaginal lubrication by the female user.

12. The method of claim 11 wherein the personal lubricant disk includes a warming ingredient and further comprises providing a warming sensation to the external vaginal tract when the personal lubricant disk is moved across the external vaginal tract.

13. The method of claim 11 wherein the personal lubricant disk includes a cooling ingredient and further comprises providing a cooling sensation to the external vaginal tract when the personal lubricant disk is moved across the external vaginal tract.

\* \* \* \* \*